United States Patent [19]

Murphy

[11] Patent Number: 4,675,382
[45] Date of Patent: Jun. 23, 1987

[54] HYBRID PROTEIN

[75] Inventor: John R. Murphy, Lexington, Mass.

[73] Assignee: President and Fellows of Harvard College, Cambridge, Mass.

[21] Appl. No.: 795,940

[22] Filed: Nov. 6, 1985

Related U.S. Application Data

[63] Continuation of Ser. No. 667,381, Nov. 1, 1984, abandoned, which is a continuation of Ser. No. 493,775, May 12, 1983, which is a continuation-in-part of Ser. No. 377,386, May 12, 1982.

[51] Int. Cl.⁴ .......................... C07K 7/10; C07K 13/00
[52] U.S. Cl. .................................... 530/350; 530/324; 530/402
[58] Field of Search ................. 260/112.5 R; 530/350, 530/324, 402

[56] References Cited

U.S. PATENT DOCUMENTS 4,082,613   4/1978   Thirumalachar et al. ............ 195/76
4,201,770   5/1980   Stevens ........................ 260/112.5 R

OTHER PUBLICATIONS

The Journal of Biological Chem. 254, No. 4 (1979) 1028–1032.
Cell vol. 22, 563–570 (1980).
Proceedings of the Nat'l. Acad. Sci. 78, no. 1 pp. 1–40.
The Journal of Biological Chem. 253, No. 19 (1978) 7109–7114.
Proc. Nat'l. Acad. Sci. 77, (1980) 3149–3153.
Nucleic Acid Res., vol. 9, No. 15, (1981) 3719–3730.

*Primary Examiner*—Delbert R. Phillips

[57] ABSTRACT

A hybrid protein including protein fragments joined together by peptide bonds, the hybrid protein including, in sequential order, beginning at the amino terminal end of the hybrid protein, (a) the enzymatically active Fragment A of diphtheria
(b) a fragment including the cleavage domain $l_1$ adjacent the Fragment A of diphtheria toxin,
(c) a fragment including at least a portion of the hydrophobic domain of Fragment B of diphtheria toxin and not including the generalized eukaryotic binding site of the Fragment B, and
(d) a fragment including a portion of a cell-specific polypeptide ligand, the portion including at least a portion of the binding domain of the polypeptide ligand, the portion of the binding domain being effective to cause the hybrid protein to bind selectively to a predetermined class of cells to be attacked by the enzymatically active Fragment A.

10 Claims, 4 Drawing Figures

HYBRID PROTEIN

This application is a continuation of Murphy U.S. patent application Ser. No. 667,381 11/11/84, now abandoned which is a continuation of U.S. patent application of Ser. No. 493,775, filed 5/12/83 which is a continuation-in-part of Murphy U.S. patent application Ser. No. 377,386, filed 5/12/82.

This invention was made in the course of work supported by the U.S. government, which has certain rights in the invention.

This invention relates to the use of recombinant DNA techniques to make hybrid protein molecules, and to the use of such molecules in the treatment of medical disorders.

The literature contains many examples of fused genes which code for hybrid proteins. For example, Villa-Komaroff et al. (1978) P.N.A.S. U.S.A. 75, 3727–3731 describes a fused gene made up of a eukaryotic structural gene fused to a non-cytoplasmic bacterial gene. The fused gene codes for a hybrid protein which is transported out of the cytoplasm.

Hybrid proteins have been also made by methods, e.g. the coupling of two different protein molecules, which do not involve recombinant DNA techniques. For example, it has been proposed to form, by coupling, therapeutic hybrid proteins consisting of a toxin coupled to a ligand capable of binding specifically to a selected class of cells. One attempt to make such a hybrid protein, reported in Chang et al. (1977) J. Biol. Chem. 252, 1515–1522, resulted in a hybrid consisting of the diphtheria toxin A chain coupled to human placental lactogen hormone by cross-linking through a disulfide bond. The hybrid protein, although it bound to cells containing lactogen receptors, did not inhibit protein synthesis in those cells.

A hybrid protein consisting of ricin A toxin coupled to the β chain of human chorionic gonadotropin hormone by similarly cross-linking through a disulfide bond has also been reported; although said to have specifity, its binding capacity has not been reported, and extremely high concentrations were required to significantly inhibit protein synthesis in rat Leydig tumor cells, making it difficult to distinguish between "non-specific" entry caused by endocytosis and "specific" entry caused by transport of the toxic portion of the hybrid across the cytoplasmic membrane of the target cells. Oeltman et al. (1979) J. Biol. Chem., 254, 1028–1032. The same shortcoming was found in a hybrid consisting of diphtheria A coupled to insulin using cystamine as the cross-linking agent. Miskimins et al. (1979) Biochem. Biophys. Res. Commun., 91, 143–151. A hybrid consisting of ricin A coupled to epidermal growth factor (EGF) by means of a heterobifunctional cross-linker has also been made, but the binding characteristics provided by the EGF are not limited to specific cells, but encompass a wide variety of cell types. Cawley et al. (1980) Cell, 22, 563–570.

It has now been found that a superior diphtheria toxin/hormone hybrid protein can be made in which the protein is synthesized as a single unit; i.e., fragments are joined together not by cross-linking but by peptide bonds.

The invention will be best understood by referring to the drawings, in which

Figure 3:
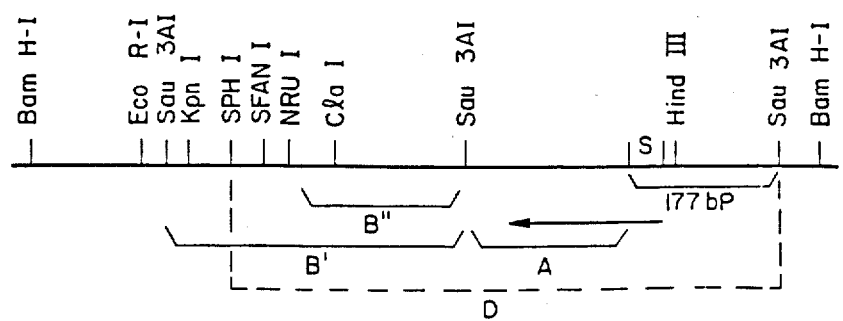
Figure 4:
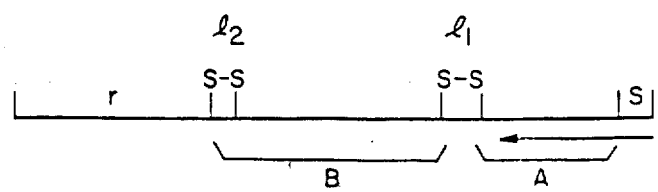

FIG. 3 is a restriction map showing the location and orientation of the diphtheria tox operon on the 3.9 kb BamH-I restriction fragment of corynephage $\beta^{tox}$ (including a site, NRU I, not found on the wild-type tox allele, but only on the mutant $tox^{228}$ allele, as will be explained in more detail below); and FIG. 4 is a diagrammatic representation of a fused gene of the invention, encoding a hybrid protein of the invention (the gene fragments are labeled in terms of the encoded protein fragments).

Figure 1:
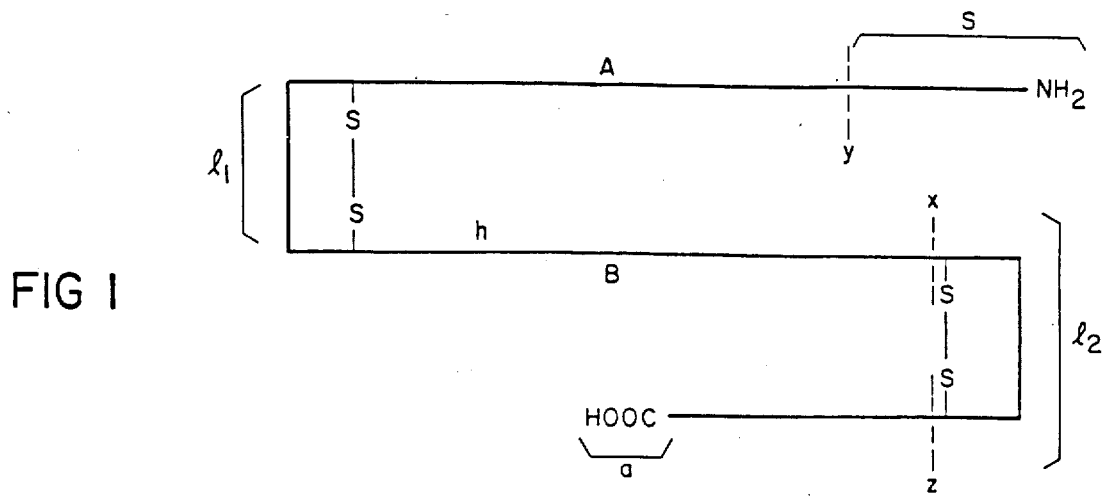
FIG. 1 is a diagrammatic representation of the diphtheria toxin molecule.

Referring to FIG. 1, the diphtheria toxin molecule consists of several functional "domains" which can be characterized, starting at the amino terminal end of the molecule, as hydrophobic leader signal sequence s, enzymatically active Fragment A, the fourteen amino acid exposed protease sensitive disulfide loop (DSL) $l_1$, containing a cleavage domain, and Fragment B, which include hydrophobic domain h, DSL $l_2$, and carboxy terminal end a.

The process by which diphtheria toxin introxicates sensitive eukaryotic cells involves at least the following steps: (i) diphtheria toxin binds to specific receptors on the surface of a sensitive cell; (ii) while bound to its receptor, the toxin molecule is internalized in an endocytic vesicle; (iii) either prior to internalization, or within the endocytic vesicle, the toxin molecule is cleaved (or processed) at a site in the region of 47,000 daltons from the N-terminal end; (iv) as the pH of the endocytic vesicle decreases to below 6, the structural intermediate form of toxin, while still bound to its receptor, is inserted into the membrane; (v) once embedded in the membrane the hydrophobic domain h forms a pore; (vi) a proteolytic cleavage in $l_1$, between Fragment A and B, occurs; (vii) thereafter, Fragment A, or a polypeptide containing Fragment A, is released into the cytosol; (viii) the catalytic activity of Fragment A, i.e., the nicotinamide adenine dinucleotide—adenosine diphosphate ribosylation of Elongation Factor 2, causes the death of the intoxicated cell. It is apparent that a single molecule of Fragment A introduced into the cytosol is sufficient to kill the cell.

The hybrid proteins of the invention include, in sequential order, beginning at the amino terminal end of the hybrid protein, the following peptide fragments joined together by peptide bonds:

(a) the enzymatically active Fragment A of diphtheria toxin (without the leader Fragment s, which is clipped during secretion of the protein), (b) a fragment including the cleavage domain $l_1$ adjacent said Fragment A of diphtheria toxin, (c) a fragment comprising at least the portion of Fragment B of diphtheria toxin encoded by the portion of the Fragment B encoding gene fragment of the tox operon between $l_1$ and the position about 90 base pairs upstream from the position on the tox operon of the NRU I site of the $tox^{228}$ allele, and (d) a fragment comprising a portion of a cell-specific polypeptide ligand, the portion including at least a portion of the binding domain of the polypeptide ligand, the portion of the binding domain being effective to cause the hybrid protein to bind selectively to a predetermined class of cells to be attacked by enzymatically active Fragment A of diphtheria toxin. The necessary portion of the toxin molecule included is depicted as the portion of the molecule between lines y and x in FIG. 1. Preferably, the hybrid protein also includes protease sensitive DSL $l_2$ of the toxin molecule, i.e. the portion of the molecule between lines x and z is also included. Line z is preferably at the point 47 amino acids from the carboxy terminal end of B', i.e., at the end of $l_2$, not closer, to ensure that the generalized eukaryotic binding site of Fragment B is excluded, so that binding will be controlled by the binding domain of the cell-specific ligand. It has been demonstrated that a little more than one-half of Fragment B must be provided for the molecule to act as an effective toxin.

Figure 2:
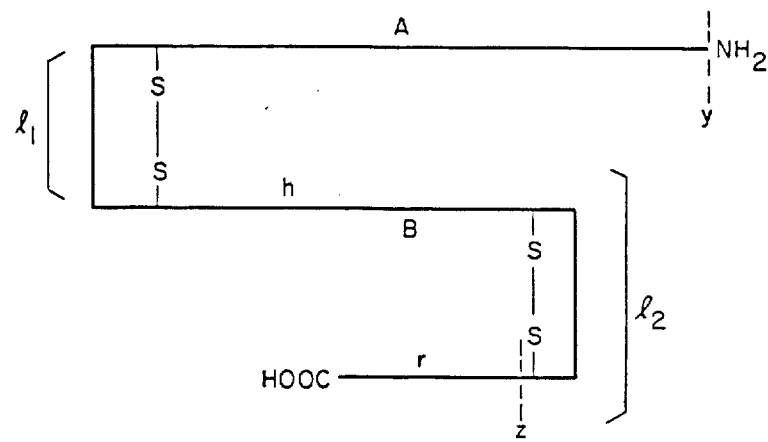
FIG. 2 is a diagrammatic representation of a hybrid protein molecule of the invention.

Referring to FIG. 2, a diagrammatic representation of a hybrid protein molecule of the invention, the y-z portion of the diphtheria toxin molecule is joined, by a peptide bond, to Fragment r of a cell-specific polypeptide ligand; i.e. a polypeptide which selectively binds to a predetermined class of cells which are to be attacked by enzymatically active Fragment A of the diphtheria toxin molecule. Fragment r can consist of the entire ligand, or a portion of the ligand which includes the entire binding domain of the ligand, or an effective portion of the binding domain.

When the ligand being used is large, it is desirable that as little of the non-binding portion as possible of the ligand be included, so that the binding domain of the molecule is positioned close to the hydrophobic domain h of Fragment B. It is also desirable to include all or most of the binding domain of the ligand molecule. In the case of α melanocyte stimulating hormone (MSH), which is a small peptide of thirteen amino acids, or βMSH, which contains seventeen amino acids, the portion of the molecule consisting of nine amino acids at the carboxy terminal end of the molecule can be used, or the entire molecule can be used.

The regions within cell-sepcific ligands in which the binding domain is located are now known for a number of such ligands. Furthermore, recent advances in solid phase polypeptide synthesis can enable those skilled in this technology to determine the binding domain of practically any such ligand, by synthesizing various fragments of the ligand and testing them for the ability to bind to the class of cells to be attacked.

The hybrid protein molecules of the invention, are virtually non-toxic to all mammalian cells except the cells of the specific class to which the ligand binding domain binds. Thus, the hybrid proteins of the invention are much more specific than many other therapeutic agents, e.g., general cytotoxic anti-cancer drugs.

The hybrid proteins of the invention, in which fragments are joined via peptide bonds, are also superior to cross-linked hybrids because the proteins of the invention can be provided in a homogeneous sample, in which all of the identical molecules are effective and selective for a particular class of cells.

The specific class of cells which are bound and attacked by the hybrid proteins of the invention is determined by the specific polypeptide ligand which supplies the binding domain of the hybrid molecule. Any cell-specific polypeptide ligand can be used which has a binding domain which is specific for a paricular class of cells which are to be attacked. Polypeptide hormones are useful such ligands. Hybrids made using a portion of the binding domain of α or βMSH, for example, selectively bind to melanocytes, rendering the hybrids useful in the treatment of melanoma. Other ligands provide different specificities; e.g., the binding domain of substance P recognizes receptors on the surfaces of neurons involved in the transmission of pain, so that hybrids made using substance P can be used to destroy such neurons to relieve chronic pain. These hybrids can also be used to map areas of the nervous system containing substance P receptors. Other specific-binding ligands which can be used include somatostatin, interleukin I, Interleukin II, and interleukin III. Interleukin II is of particular importance because of its role in allergic reactions and autoimmune diseases such as lupus, involving activated T cells. In addition, since all of the interleukins are specific for T cells, hybrids made with them could be used to treat cancers involving the immune system, and to inhibit the rejection of transplanted organs. Other useful polypeptide ligands having cell-specific binding domains are follicle stimulating hormone (specific for ovarian cells); luteinizing hormone (specific for ovarian cells); thyroid stimulating hormone (specific for thyroid cells); vasopressin (specific for uterine cells, as well as bladder and intestinal cells); prolactin (specific for breast cells); and growth hormone (specific for certain bone cells).

The hybrid proteins of the invention are preferably prepared using recombinant DNA techniques involving forming the desired fused gene coding for the hybrid protein, and then expressing the fused gene, using conventional procedures. Referring to FIG. 3, the location and orientation of the diphtheria tox operon on the 3.9 kb BamH-I restriction fragment of corynephage $\beta^{tox+}$ allows the tox operon to be cleaved at a desired location, and the desired portion of the operon to be fused with the desired portion of the gene for a selected polypeptide ligand. A more detailed description of the tox operon, and a description of the cloning of Fragment A, are contained in Leong et al. (1983) Science 220, 515, hereby incorporated by reference. Fragment A, cloned as described therein to make plasmid pDT201, was deposited in the American Type Culture Collection, Rockville, MD on May 11, 1983, and has been given ATCC Accession No. 39359.

Referring to FIGS. 3 and 4, the portion of the diphtheria tox operon (FIG. 3) used to make the fused gene (FIG. 4) encoding the hybrid proteins of the invention is preferably the portion indicated by the dotted lines delineating Fragment D; i.e. the portion of the tox gene from the first Sau 3AI site to the SPH I site. Fragment D thus includes the 831 base pair (bp) gene fragment encoding Frament A (including the 177 bp sequence ahead of the structural gene which includes the promoter and the portion encoding the signal sequence, S in FIG. 1); the portion of the gene fragment encoding the hydrophobic domain of Fragment B; and the gene fragment encoding DSL $l_2$.

As shown in FIG. 3, the first 177 bp of the gene fragment encoding Fragment A includes, ahead of the tox promoter, some DNA which is not part of the tox operon. This DNA is irrelevant and is not transcribed; it is included only because the Sau 3AI site at the start of the Fragment A encoding gene fragment is the most convenient restriction site near the tox promoter (which is depicted as the line just to the left of Hind III).

It should be possible to obtain Fragment D by simply excising it from the tox operon via cleavage at Sau 3AI and SPH I. Alternatively, gene fragments can be fused together as follows. First the gene fragment encoding Fragment A is obtained. Next, the gene fragment encoding most of Fragment B, from Sau 3AI to Sau 3AI (B' of FIG. 3) is obtained. The gene fragment encoding Fragment B' has been cloned in plasmid pUC8, to make plasmid pDT301, and was deposited in the American Type Culture Collection, Rockville, MD on May 11, 1983, and was given ATCC Accession No. 39360. Fragment B' is cut back, using enzyme Bal31, about 200 bp, to the position of the NRU I site on tox$^{228}$ (the wild-type tox allele does not have an NRU I site), to give B'' (FIG. 3). Fragments A and B'' are fused, a fragment encoding $l_2$ is fused to B'', and a fragment encoding the desired portion of the polypeptide ligand is fused to $l_2$.

In the above scheme, the Fragment B' encoding gene fragment is preferably cut back to the precise location of NRU I, but can also be cut back to any location between the location 90 bp ahead of NRU I, and the end of the $l_2$ encoding region, (i.e., within the 208 bp region between the location 90 bp ahead of NRU I, and the beginning of the $l_2$ encoding region). Or, the B' encoding fragment could be cut back to the carboxy terminal end of the $l_2$ encoding region (129 bp downstream from NRU I), in which case fusion of a synthetic $l_2$ encoding region is unnecessary. (It should be evident that, when the B' encoding region is cut back and a synthetic $l_2$ encoding fragement is fused to it, there generally will be a small number of base pairs normally found between NRU I and SPH I which will not be present in the fused gene, so that, strictly speaking, not all of D of FIG. 3, or all of y-z of FIGS. 1 and 2, will necessarily be included.)

An alternative method, less preferred than the scheme above, is to fuse the ligand-encoding gene fragment directly to B'', without employing the $l_2$ encoding fragment.

The fused gene, either including or omitting the $l_2$-encoding fragment, can alternatively be made using the B'' encoding gene fragment from the mutant tox$^{228}$ allele, rather than the wild-type allele. The tox$^{228}$ allele, containing the NRU I site, is easily processed to yield the B'' encoding fragment. The tox$^{228}$ allele is described in Uchida et al. (1973) Jour. Biolog. Chem. 248, 3831, hereby incorporated by reference.

In more detail, fused genes encoding hybrid proteins of the invention can be made as follows.

Vectors

The preferred vectors are plasmids pUC7, pUC8, pUC9, and pRR322. The pUC plasmids, described in Viera et al. (1982) Gene 19, 259 (hereby incorporated by reference) are particularly well-suited for double digest cloning, a procedure which permits the fused genes to be made unambiguously.

Fused gene

Below is a flow chart for constructing diphtheria toxin-MSH fused genes containing the protease sensitive loop $l_2$ between the tox sequences and the ligand (in this case, MSH) sequences.

(i) pDT201 $\xrightarrow{\text{Sau3A1 digest}}$ purify Sau3A1-2 (Fragment A)

(ii) pDT301 $\xrightarrow{\text{HindIII digest}}$ $\xrightarrow{\text{Bal31 cutback}}$ $\xrightarrow{\text{PstI linkers}}$ -continued $\xrightarrow{\text{Sau3A1 digest}}$ $\xrightarrow{\text{reclone Sau3A1-PstI in pUC8}}$ Select blue colonies on X-G for proper reading frame $\longrightarrow$ purify Sau3A1-PstI (Fragment B'')

(iii) in vitro synthesis of protease sensitive loop $l_2$ (PstI-loop-EcoR1) $\longrightarrow$ clone into PstI-EcoR1 sites on pUC9 & purify fragment (iv) clone (ii) Sau3A1-PstI and (iii) PstI-Eco into the BamH1-EcoR1 sites on pCU8 (Sau3A1-Fragment B''-loop-EcoR)

(v) clone (iv) Sau3A1-EcoR1 and MSH sequence into the BamH1 site on pUC8 (Sau3A1-Fragment B''-loop-MSH-BamH1)

(vi) clone (i) Sau3A1-Fragment A-Sau3A1 and (v) Sau3A1-Fragment B''-loop-MSH-BamH1 into the BamH1 site on pUC8 (Sau3A1-Fragment A-Fragment B''-loop-MSH-BamH1)

Referring to the above flow chart, in step (i), the Fragment A encoding gene fragment is first obtained and purified, as described in Science, Id. In step (ii) the Fragment B'' encoding fragment is obtained by cutting back a larger Fragment B' encoding region using the enzyme Bal31.

As shown in FIG. 3 the gene fragment encoding Fragment B' is the 1,023 bp region between two Sau 3AI sites, the first of which is at the DNA sequence encoding the third arginine in $l_1$, and the second of which is 49 bp before the end of the tox structural gene. The gene fragment encoding B' has, as is mentioned above, been cloned in pUC8. The plasmid carrying this fragment in the same orientation as the lac Z gene has been designated pDT301; (the lac Z and B' genes are out of frame on pDT301).

Referring again to the above flow chart, pDT301 is opened via HindIII digestion and then the B' encoding fragment is cut back by exposure to the exonuclease Bal31 for varying time periods. The ends of the resulting shortened gene fragments (of varying lengths) are then blunt-end ligated with EcoR1 and PstI linkers and the fragments are then digested with SauR1. This results in a heterogenous (in terms of size) population of gene fragments encoding part of B'.

These fragments are then recloned in either the BamH1-PstI or the BamH1-EcoR1 sites of pUC8. Cloning in these sites allows selection only of clones having BamH1 (Sau 3AI) on one end and PstI or EcoR1 on the other. Also, cloning in double digested pUC8 allows for only one fragment orientation, and selection of blue colonies (those expressing lac Z) on X-G plates verifes an in-frame junction between the shortened B' encoding region and lac Z. The preferred clones are those in which the B' encoding region is 830 bp long; i.e. the gene has been cut back 200 bp, to the position of NRU I on tox$^{228}$.

The next step (iii) is the in vitro synthesis of the gene fragment encoding the protease sensitive loop $l_2$. This is carried out by means of conventional solid phase oligonucleotide synthesis. The sequence of this fragment, including the PstI and EcoR1 linkers which are attached after synthesis, is shown below:

```
    Cys—Arg—Ala—Ile—Asp—Gly—Asp—Val—Thr—Phe—Cys
    TGC—AGA—GCT—ATA—GAG—GGT—GAT—GTA—ACT—TTT—TGC
Pst1                                                    EcoR1
linker                                                  linker
```

The next step (iv) is to clone the B" encoding fragment from step (ii) and the $l_2$ encoding fragment from step (iii) into BamH1-EcoR1 sites on pUC8.

Next, the desired fragment encoding a portion of the cell-specific ligand is provided, either from a natural source or by oligonucleotide synthesis. For example, gene fragments encoding specific binding portions of α and βMSH can be synthesized via conventional solid phase oligonucleotide synthesis.

The DNA sequences of those gene fragments, along with the appropriate linkers, are shown below:

αMSH:
```
       Ser—Tyr—Ser—Met—Glu—His—Phe—Arg—Trp—Gly—Lys—Pro—Val
    AGC—TAT—AGC—ATG—GAA—CAT—TTT—AGA—TGG—GGX—AAA—CCX—GTX
     T   C   T           G   C   C   G               G
EcoR1                                              stop codon &
Linker                                             BamH1 linker
```

βMSH
```
       Asp—Glu—Gly—Pro—Tyr—Met—Glu—His—Phe—
    GAT—GAA—GGT—CCA—TAT—ATG—GAG—CAC—TTT
     C   G   X   X   C       A   T   C

Arg—Trp—Gly—Ser—Pro—Pro—Lys—Asp
    AGA—TGG—GGT—TCT—CCG—CCG—AAA—GAT
     G   X   X   X   X   TC      C
EcoR1                           stop codon &
linker                          BamH1 linker
```

The unique Pst1 and EcoR1 sites of pUC8 permit the subcloning of either of the above synthetic MSH sequences, downstream from the $l_2$ encoding fragment.

Finally (step vi) the Fragment A encoding gene fragment is fused to the gene fragment encoding B"—1-2—MSH, to complete the gene fusion as illustrated in FIG. 4 (labeled in terms of encoded protein fragments), which codes for a hybrid protein which selectively binds to and attacks a selected class of cells (in this case, melanocytes).

Another example of a suitable polypeptide ligand is substance P, the utility of which is described above. A fused gene containing the substance P gene, rather than the α or βMSH gene, is made basically as outlined above. The substance P gene is synthesized using conventional sold phase oligonucleotide synthesis. The substance P gene sequence is: CGTCCTAAACCT-CAGCAGTTCTTCGGTCTGATG.

As is clear from the above, the portion of the genetic sequence for the polypeptide ligand must be sufficient to enable the corresponding amino acid sequence to cause the hybrid protein to bind to the predetermined class of cells. Preferably, the gene for the polypeptide hormone will include all or most of the genetic sequence for the binding domain of the ligand.

Generally, as in the above examples, the manipulative operations are carried out using cloning vectors; e.g., phages or plasmids. The genetic material coding for the binding domain of the polypeptide ligand can be either cloned DNA or a synthetic oligonucleotide sequence, whichever is more convenient for the particular ligand gene employed. Generally the fused gene will reside on a cloning vector, e.g., a plasmid or a phage, which is used to transform cultured microorganisms. The hybrid protein is then harvested from the culture media of the cells using conventional techniques.

The hybrid proteins of the invention are administered to a mammal, e.g., a human, suffering from a medical disorder, e.g., cancer, characterized by the presence of a class of unwanted cells to which a polypeptide ligand can selectively bind. The amount of protein administered will vary with the type of disease, extensiveness of the disease, and size of species of the mammal suffereing from the disease. Generally, amounts will be in the range of those used for other cytotoxic agents used in the treatment of cancer, although in certain instances lower amounts will be needed because of the specificity of the hybrid proteins.

The hybrid proteins can be administered using any conventional method; e.g., via injection, or via a timed-release implant. In the case of MSH hybrids, topical creams can be used to kill primary cancer cells, and injections or implants can be used to kill metastatic cells. The hybrid proteins can be combined with any non-toxic, pharmaceutically-acceptable carrier substance.

What is claimed is:

1. A hybrid protein comprising protein fragments joined together by peptide bonds, said hybrid protein comprising, in sequential order, beginning at the amino terminal end of said hybrid protein,
   (a) the enzymatically active Fragment A of diphtheria toxin,
   (b) a fragment including the cleavage domain $l_1$ adjacent said Fragment A of diphtheria toxin,
   (c) a fragment comprising at least a portion of the hydrophobic domain of Fragment B of diphtheria toxin and not including the generalized eukaryotic binding site of said Fragment B, and
   (d) a fragment comprising a portion of a cell-specific polypeptide ligand, said portion including at least a portion of the binding domain of said polypeptide ligand, said portion of said binding domain being effective to cause said hybrid protein to bind selectively to a predetermined class of cells to be attacked by said enzymatically active Fragment A.

2. The hybrid protein of claim 1 wherein said fragment (c) is encoded by the portion of the diphtheria toxin Fragment B encoding gene fragment between $l_1$ and the position of the NruI site.

3. The hybrid protein of claim 2, further comprising fragment $l_2$ between fragments (c) and (d).

4. The hybrid protein of claim 1 wherein said hybrid protein is coded for by a fused gene comprising regions coding for said protein fragments.

5. The hybrid protein of claim 1 wherein said polypeptide ligand is a hormone.

6. The hybrid protein of claim 5 wherein said portion of said polypeptide hormone is a portion of $\alpha$ or $\beta$ melanocyte stimulating hormone effective to cause said hybrid protein to bind to malignant melanocyte cells.

7. The hybrid protein of claim 5 wherein said portion of said polypeptide hormone is a portion of substance P effective to cause said hybrid protein to bind to pain receptor neurons.

8. The hybrid protein of claim 5 wherein said portion of said polypeptide hormone is a portion of interleukin I effective to cause said hybrid protein to bind to T cells.

9. The hybrid protein of claim 5 wherein said portion of said polypeptide hormone is a portion of interleukin II effective to cause said hybrid protein to bind to T cells.

10. The hybrid protein of claim 5 wherein said portion of said polypeptide hormone is a portion of interleukin III effective to cause said hybrid protein to bind to T cells.

* * * * *

UNITED STATES PATENT AND TRADEMARK OFFICE
CERTIFICATE OF CORRECTION

PATENT NO. : 4,675,382
DATED : June 23, 1987
INVENTOR(S) : John R. Murphy

It is certified that error appears in the above-identified patent and that said Letters Patent are hereby corrected as shown below:

In claim 3, line 1, change "claim 2" to --claim 1 or claim 2--.

Signed and Sealed this

Twenty-first Day of June, 1988

Attest:

DONALD J. QUIGG

Attesting Officer

Commissioner of Patents and Trademarks